(12) United States Patent
Crutchley et al.

(10) Patent No.: US 11,744,799 B2
(45) Date of Patent: Sep. 5, 2023

(54) TOPICAL COMPOSITION (71) Applicant: MC2 Therapeutics Limited, Leatherhead (GB)

(72) Inventors: Nigel Crutchley, Leatherhead (GB); Michelle Georgiou, Leatherhead (GB)

(73) Assignee: MC2 Therapeutics Limited, Leatherhead Surrey (GB)

(*) Notice: Subject to any disclaimer, the term of this patent is extended or adjusted under 35 U.S.C. 154(b) by 758 days.

(21) Appl. No.: 16/482,177

(22) PCT Filed: Jan. 30, 2018

(86) PCT No.: PCT/GB2018/050263
§ 371 (c)(1),
(2) Date: Jul. 30, 2019

(87) PCT Pub. No.: WO2018/142117
PCT Pub. Date: Aug. 9, 2018

(65) Prior Publication Data
US 2022/0110868 A1    Apr. 14, 2022

(30) Foreign Application Priority Data
Jan. 31, 2017 (GB) .................................. 1701583

(51) Int. Cl.
| A61K 9/107 | (2006.01) |
| A61K 9/00 | (2006.01) |
| A61K 31/69 | (2006.01) |
| A61K 47/10 | (2017.01) |
| A61K 47/14 | (2017.01) |
| A61K 47/44 | (2017.01) |

(52) U.S. Cl.
CPC .......... *A61K 9/107* (2013.01); *A61K 9/0014* (2013.01); *A61K 31/69* (2013.01); *A61K 47/10* (2013.01); *A61K 47/14* (2013.01); *A61K 47/44* (2013.01)

(58) Field of Classification Search
CPC ...... A61K 9/107; A61K 9/0014; A61K 31/69; A61K 47/10; A61K 47/14; A61K 47/44
See application file for complete search history.

(56) References Cited

U.S. PATENT DOCUMENTS

| 4,486,333 | A | 12/1984 | Sebba |
| 5,573,757 | A | 11/1996 | Riess et al. |
| 8,501,712 | B2 | 8/2013 | Baker et al. |
| 10,265,265 | B2 * | 4/2019 | Wheeler ............ A61K 31/573 |
| 11,065,195 | B2 * | 7/2021 | Wheeler ............ A61K 9/0014 |
| 2006/0239947 | A1 | 10/2006 | Dias et al. |
| 2008/0227759 | A1 | 9/2008 | Wheeler et al. |
| 2008/0234239 | A1 * | 9/2008 | Wheeler ............ A61K 31/59 514/167 |
| 2016/0318955 | A1 | 11/2016 | Akama |
| 2017/0152273 | A1 * | 6/2017 | Merchant ........... A61K 47/06 |
| 2019/0060288 | A1 | 2/2019 | Crutchley |
| 2021/0015831 | A1 | 1/2021 | Crutchley |
| 2021/0275554 | A1 | 9/2021 | Crutchley |

FOREIGN PATENT DOCUMENTS

| EP | 1706087 A1 * | 10/2006 | ............ A61K 8/046 |
| EP | 1970048 A1 * | 9/2008 | ............ A61K 31/59 |
| EP | 1970048 A1 | 9/2008 | |
| JP | 2016-501209 A | 1/2016 | |
| WO | WO 97/32559 | 9/1997 | |
| WO | 2007095638 A2 | 8/2007 | |
| WO | 2008/110826 A1 | 9/2008 | |
| WO | WO-2011017274 A2 * | 2/2011 | ............ A61K 8/64 |
| WO | 2017102565 A1 | 6/2017 | |
| WO | WO 2017/093857 A1 | 6/2017 | |
| WO | 2018031655 A1 | 1/2018 | |
| WO | 2018142117 A1 | 8/2018 | |

OTHER PUBLICATIONS

Tsutomu Akama, et al, Discovery and Structure-Activity Study of a Novel Benzoxaborole Anti-Inflammatory Agent (AN2728) for the Potential Topical Treatment of Psoriasis and Atopic Dermatitis, 19 Bioorg. Med. Chem. Let. 2129 (Year: 2009).*

Tustomu Akama, et al, Discovery an Structure-Activity Study of a Novel Benzoxaborole Anti-Inflammatory Agent (AN2728) for the Potential Topical Treatment of Psoriasis and Atopic Dermatitis, 19 Bioorg. Med. Chem. Let. 2129 (Year: 2009).*

Kurt Jarnagin, et al., Crisaborole Topical Ointment, 2%: A Nonsteroidal, Topical, Anti-Inflammatory Phosphodiesterase 4 Inhibitor in Clinical Development for the Treatment of Atopic Dermatitis, 15 J Drug Dermatol. 390 (Year: 2016).*

Israeli Office Action for IL Application No. 268374 dated Nov. 30, 2021 (7 pages, with English translation).

Ip et al., "Formulation Skin Penetration, and Anit-Inflammatory Activity of AN2728: A Novel Borinic Acid Ester," J. Am Acad Dermatol., 2008, 56(2):AB1777.

International Preliminary Report on Patenatbility for PCT/GB2018/050263 dated Aug. 15, 2019.

G. Godwin, Harry's Cosmeticology 7th Edition (1982).

Mollison et al., "A macrolactam inhibitor of T helper type 1 and T helper type 2 cytokine biosynthesis for topical treatment of inflammatory skin diseases", J Invest Dermatol., 112(5):729-38 (1999).

Sebba, "Biliquid Foams—A Preliminary Report", J. Colloid and Interface Science, 40:2, 468-474 (1972).

Sebba, "The Behaviour of Minute Oil Droplets Encapsulated in a Water Film", Colloid Polymer Sciences, 257, 392-396 (1979).

Hicks, "Investigating the Generation, Characterisation Structure of Biliquid Foams", PhD Thesis, University of Bristol (2005).

Crutchley, "The Encapsulation of Oils and Oil Soluble Substances Within Polymer Films", PhD Thesis, The University of Leeds (2006).

Lye and Stuckey, "Structure and stability of colloidal liquid aphrons," Colloid and Surfaces, 131, 119-136 (1998).

(Continued)

*Primary Examiner* — Sean M Basquill
(74) *Attorney, Agent, or Firm* — Merchant & Gould P.C.

(57) ABSTRACT

The present invention relates to a composition for topical application comprising a polyaphron dispersion, wherein the polyaphron dispersion comprises a continuous phase, a discontinuous phase and crisaborole.

19 Claims, 2 Drawing Sheets

(56) References Cited

OTHER PUBLICATIONS

Zane et al. "Crisaborole and its potential ole in treating atopic dermatitis: overview of early clinical studies." Immunotherapy, vol. 8, No. 8, Future Medicien, published online Jun. 10, 2016, https://doi.org/10.2217/imt-2016-0023.
First Examination Report from Indian Application No. 201947029785, dated Jan. 24, 2020.
Karkevich D.A., Pharmacology, Textbook—9th Ed., revised, add. and correct.—M.:GEOTAR-Media, 2008, pp. 66-67.
Beutner et al., "P3327 AN2728 demonstrates significant efficacy in three phases ib psoriasis microplaque trails", Journal of the American Academy of Dermatology, vol. 60, No. 3, Mar. 2009, pp. AB168.
Ip et al., "P2756 Preclinical toxicology of AN2728, a novel borinic acid ester with anti-inflammatory activity", Journal of the American Academy of Dermatology, vol. 56, No. 2, Feb. 2007, pp. AB188.
L. Eichenfield, "Long-term safety of crisaborole topical ointment, 2%, in atopic dermatitis", Journal of Investigative Dermatology, vol. 136 (5): S49.
T. Akama et al., "Discovery and structure-activity study of a novel benzoxaborole anti-inflammatory agent (AN2728) for the potential topical treatment of psoriasis and atopic dermatitis", Bioorganic & Medicinal Chemistry Letters vol. 19 (8) (2009).
International Search Report and Written Opinion for PCT/GB2018/050263 dated Apr. 9, 2018.
Search Report for British Patent Application No. 1701583.5, dated Oct. 25, 2017.
Office Action for Korean Patent Application No. 10-2019-7025209 dated Sep. 20, 2022, 8 pages.

\* cited by examiner

TOPICAL COMPOSITION

This application is a National Stage Application of PCT/GB2018/050263, filed 30 Jan. 2018, which claims the benefit of priority to British Patent Application No. 1701583.5, filed 31 Jan. 2017, which applications are incorporated herein by reference. To the extent appropriate, a claim of priority is made to each of the above disclosed applications.

The present invention relates to a topical composition. In particular, the invention relates to a topical composition comprising crisaborole having improved skin permeation, stability and/or patient compliance compared to existing crisaborole formulations.

Atopic dermatitis is a common, chronically relapsing, inflammatory skin disease. The exact cause of the disease is a matter of debate but it is characterised by eczematous lesions, dry skin and intense pruritus (itching). There is also strong evidence that the prevalence of atopic dermatitis has been increasing over recent years. The condition can vary from mild to severe with subsequent detriment to quality of life.

Current treatment programs include the use of emollient creams and then supplementing this with other therapies on a graduated scale. Topical application of a mild corticosteroid such as hydrocortisone acetate is usually the next step, with increasingly potent corticosteroids being utilised only if necessary. There are, however, a number of potential drawbacks associated with topical corticosteroids. These drawbacks, which apply especially to the more potent corticosteroids, can include skin thinning, tachyphylaxis and rebound phenomena. Due to these and other potential side effects, corticosteroids are not advised for use on the facial areas. This is despite the fact that atopic dermatitis that develops on the face can be the most detrimental to a patient's quality of life.

Recently, crisaborole has been approved by the US Food and Drug Administration (FDA) for the treatment of mild to moderate atopic dermatitis in patients of at least two years of age. Crisaborole is a non-steroidal topical phosphodiesterase-4 (PDE-4) inhibitor. While its mechanism of action is not yet fully understood, it is believed that crisaborole inhibits PDE-4 in target cells. This, in turn, is thought to reduce the production of pro-inflammatory cytokines thought to cause the signs and symptoms of atopic dermatitis. Crisaborole is also being developed for other inflammatory dermatological conditions such as psoriasis.

The FDA-approved crisaborole formulation (trade name Eucrisa®) is a non-aqueous topical ointment having a crisaborole level of 2%. The absence of water limits the chances of chemical degradation due to hydrolysis or pH incompatibility and the occlusive nature of the bulk of the excipients creates a high degree of occlusion aiding permeation of the active. However, like most ointments, the lack of water and the presence of paraffin and wax components give the formulations a poor aesthetic profile (S. E. Wolverton, Comprehensive Dermatologic Drug Therapy $3^{rd}$ Edition (2012), p 13). This can potentially limit patient compliance.

US 2016/0318955 A1 discloses boron-containing small molecules as anti-inflammatory agents, and exemplifies crisaborole. The document further suggests that the boron compounds disclosed therein can be formulated into creams, and provides examples of cream formulations containing some boron-containing small molecules but not crisaborole itself. Creams are advantageous over non-aqueous ointments in the sense that they generally have a better aesthetic profile and elicit improved patient compliance. However, US 2016/0318955 A1 makes no mention of the physical/chemical stability of the creams or whether the drug remains in solution. It is believed that crisaborole would have a tendency to crystallise out of the cream formulations disclosed in US 201610318955 A1, particularly when present at a relatively high concentration (e.g. 2%). This could, in turn, give rise to physical instability of the formulation. Poor solvation of the crisaborole may also have a negative effect on skin permeation, and indeed US 2016/0318955 A1 makes no mention of whether the vehicle mediates sufficient skin penetration.

Accordingly, it is one object of the present invention to provide a formulation that can deliver crisaborole into the skin with better aesthetics than prior art ointment formulations. In other words, it is one object of the present invention to provide a crisaborole formulation having better patient compliance than prior art ointment formulations.

It is an alternative and/or additional object to provide a crisaborole formulation having better skin penetration than prior art cream and/or ointment formulations or at least provide a commercially useful alternative thereto.

It is an alternative and/or additional object to provide a cream formulation in which the crisaborole is fully solvated or at least more solvated than in existing cream formulations.

It is an alternative and/or additional object to provide a cream formulation having improved chemical and/or physical stability in comparison with existing cream formulations.

According to a first aspect, the present invention provides a composition for topical application comprising a polyaphron dispersion, wherein the polyaphron dispersion comprises a continuous phase, a discontinuous phase and crisaborole.

Such compositions can be provided in the form of an aqueous cream, giving an improved aesthetic profile relative to the non-aqueous ointments of the prior art. This can improve patient compliance. Moreover, unlike the creams of the prior art, the compositions as described herein can incorporate a significant quantity (e.g. 2-3 wt %) of crisaborole in fully solubilised form (i.e. the crisaborole is not present as solid particulates or crystals). Because the crisaborole has less of a tendency to precipitate out than in the creams of the prior art, physical stability and/or skin permeation can be improved.

The present invention will now be described further. In the following passages different aspects/embodiments of the invention are defined in more detail. Each aspect/embodiment so defined may be combined with any other aspect/embodiment or aspects/embodiments unless clearly indicated to the contrary. In particular, any feature indicated as being preferred or advantageous may be combined with any other feature or features indicated as being preferred or advantageous.

The present invention provides a composition for topical application. A composition for topical application is defined herein as a composition that is suitable for direct application to a part of the human or animal body. Preferably, the composition is suitable for direct application to the skin, for example the face, scalp, feet, limbs or trunk.

The composition of the present invention comprises a polyaphron dispersion. By polyaphron dispersion as used herein it is meant a particular kind of hydrophilic liquid-in-hydrophobic liquid or hydrophobic liquid-in-hydrophilic liquid dispersion comprising (a) a hydrophilic liquid miscible phase, (b) a second hydrophobic phase being immiscible or substantially immiscible with the first phase and (c) one or more surfactants, wherein the dispersed or discontinuous phase is in the form of small (e.g. micron to sub-micron diameter, but more usually at least 1 micron diameter) droplets, and the whole having the following characteristics, which distinguish polyaphron dispersions from conventional or common emulsions and other dispersion types:

1. They are capable of existing in a stable form wherein the volume fraction of the dispersed phase ($\phi_{ip}$) is greater than 0.7 and can be as high as 0.97. ($\phi_{ip}$ is the volume ratio of discontinuous to continuous phase expressed as a fraction).
2. The microscopic appearance of polyaphron dispersions where $\phi_{ip}$ is greater than 0.7 is that of an aggregate of individual droplets, pushed closely together into polyhedral shapes, resembling the appearance of a gas foam. In this form, the dispersion has gel-like properties and is referred to as a Gel Polyaphron Dispersion (GPD).
3. Stable polyaphron dispersions can be formed with a surfactant concentration less than 3% and more typically less than 2% by weight of the total composition.
4. Gel Polyaphron Dispersions (as described in 2 above) can be diluted to any extent by the addition of more continuous phase without the addition of more surfactant, when the gel-like properties disappear. Once $\phi_{ip}$ has been reduced to below 0.7, the individual droplets of internal phase become separated to take the form of spherical droplets, which remain stable and intact but which may nevertheless join together in loose associations and float to the top or sink to the bottom of the diluted dispersion (depending on the relative densities of the two phases). In this diluted form each droplet is referred to as a Colloidal Liquid Aphron (CLA). Simple shaking of the diluted dispersion instantly causes a homogeneous, stable dispersion of Colloidal Liquid Aphrons to re-form.

Each of the above characteristics and a combination of them clearly differentiate the polyaphron dispersions of the present invention from conventional emulsions and other dispersion types which do not have all of those characteristics. Polyaphron dispersions are disclosed in the following literature references by Sebba: "Biliquid Foams", J. Colloid and Interface Science, Q (1972) 468-474 and "The Behaviour of Minute Oil Droplets Encapsulated in a Water Film", Colloid Polymer Sciences, 257 (1979) 392-396, Hicks "Investigating the Generation, Characterisation, and Structure of Biliquid Foams", PhD Thesis, University of Bristol, 2005, Crutchley "The Encapsulation of Oils and Oil Soluble Substances Within Polymer Films", PhD Thesis, The University of Leeds, 2006 and Lye and Stuckey, Colloid and Surfaces, 131 (1998) 119-136. Aphrons are also disclosed in U.S. Pat. No. 4,486,333 and WO 97/32559.

Polyaphron dispersions are sometimes referred to as 'Biliquid Foams', 'High Internal Phase Emulsions (HIPEs)', 'High Internal Phase Ratio Emulsions (HIPREs)' and 'Gel Emulsions'. In U.S. Pat. No. 5,573,757 a composition comprising a polyaphron dispersion is described as "a viscoelastic gel". All descriptions that refer to dispersions having the characteristics described above are polyaphron dispersions as used in the present invention.

The polyaphron dispersion comprises a continuous phase and a discontinuous phase. In other words, the composition comprises a dispersion of a discontinuous phase in a continuous phase. The phases are physically distinct. Preferably, the discontinuous phase comprises an oil and the continuous phase is aqueous. The inclusion of an aqueous phase in the present composition enables it to be provided in the form of a lotion or cream, as opposed to an ointment. Thus, the present composition has an improved aesthetic profile relative to the ointments of the prior art, thereby improving patient compliance. Preferably, the composition is in the form of a lotion or cream.

Preferably, the oil is a pharmaceutically acceptable oil. Examples of oils which may be used in the present invention include coconut oil, squalane, isopropyl myristate, isopropyl isostearate, isopropyl palmitate, modified triglycerides, caprylic capric glycerides, fractionated triglycerides, glyceryl tricaprate, glyceryl tricaproate, glyceryl tricaprylate, glyceryl tricaprylate/caprate, glyceryl tricaprylate/caprate, glyceryl tricaprylate/caprate/laurate, glyceryl tricaprylate/caprate/linoleate, glyceryl tricaprylate/capratelstearate, glyceryl trilaurate, glyceryl trilinoleate, glyceryl trilinolenate, glyceryl trioleate, glyceryl triundecanoate, linoleic glycerides, saturated polyglycolized glycerides, synthetic medium chain triglyceride containing primarily $C_8$-$C_{12}$ fatty acid chains, medium chain triglycerides, long chain triglycerides, modified triglycerides, fractionated triglycerides, isostearyl isostearate, diisopropyl adipate, mineral oil, dimethicone, cyclomethicone, hydrogenated polyisobutene, heptamethytnonane, and mixtures thereof. Further examples of oils which may be used in the present invention include dibutyl adipate, diethyl sebacate, castor oil, oleic acid, oleyl alcohol, and mixtures thereof, optionally in a mixture with one or more of the aforementioned oils. Preferably, the composition does not comprise a wax component that is solid at 25° C.

Figure 1:
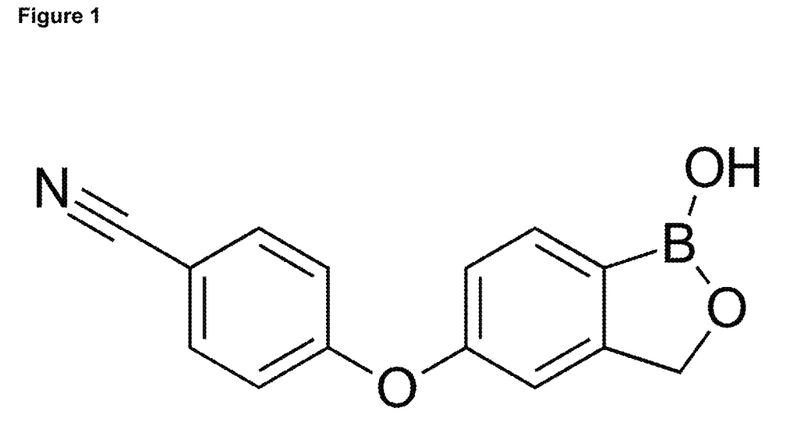
FIG. 1 depicts the chemical structure of crisaborole.

The polyaphron dispersion comprises crisaborole. The chemical structure of crisaborole is depicted in FIG. 1. The source of crisaborole is preferably anhydrous crisaborole, although it will be appreciated that other sources of crisaborole may be used. In particular, the term "crisaborole" as used herein encompasses the free acid, salts (such as pharmaceutically acceptable salts), prodrugs, solvates and hydrates thereof. However, the amounts of crisaborole to be incorporated into the compositions described herein are based on the anhydrous form of crisaborole. It would be within the capabilities of the skilled person to adjust the quantity used in the preparation of the composition depending on the source used to provide the desired amount in the final composition.

Preferably, the crisaborole is present in an amount of from 1 to 5 wt % by weight of the composition, more preferably from 1.5 to 5 wt %, still more preferably from 2 to 4 wt % still more preferably from 2 to 3.5 wt %, and most preferably from 2.5 to 3.5 wt %. The present inventors have found that the present invention enables crisaborole to remain fully solvated in the composition even when it is present at relatively high concentrations. Preferably at least 95 wt % of the crisaborole is dissolved in the composition, more preferably at least 98 wt %, and most preferably at least 99 wt %. In other words, preferably at least 95 wt % of the crisaborole is in solution in the composition, more preferably at least 98 wt %, and most preferably at least 99 wt %. Preferably, the crisaborole is dissolved at these levels throughout a temperature range of from 4 to 20° C.

Preferably, the crisaborole is predominantly in the discontinuous phase. Alternatively, the crisaborole may be predominantly in the continuous phase. By 'predominantly' it is meant that at least 90 wt % of the crisaborole in the composition is present in the discontinuous or continuous phase as appropriate, preferably at least 95 wt %, and more preferably at least 99 wt %.

One strategy developed by the inventors for achieving good solvation of the crisaborole at high crisaborole concentrations is to use a high oil loading and/or a particular combination of oils to solvate the crisaborole in the discontinuous phase. Thus, in some embodiments, the discontinuous phase is present in an amount of at least 40 wt % by weight of the composition, preferably at least 50 wt %, more preferably at least 60 wt %, still more preferably at least 65 wt %, and most preferably at least 70 wt %. In these embodiments, the crisaborole is preferably predominantly in the discontinuous phase.

In these embodiments, the discontinuous phase comprises an oil. Preferably, the oil is present in an amount of at least 40 wt % by weight of the composition, preferably at least 50 wt %, preferably at least 60 wt %, still more preferably at least 65 wt %, and most preferably at least 70 wt %. In these embodiments, the continuous phase preferably comprises less than 10 wt %, preferably less than 5 wt %, more preferably less than 2 wt %, and most less than 1 wt % by weight of the composition of a polar water-miscible solvent selected from the group consisting of $C_1$-$C_4$ alcohols, polyethylene glycol, ethylene glycol, propylene glycol, butylene glycol, pentylene glycol, glycerol, diethylene glycol mono ethyl ether, propylene carbonate and mixtures of two or more thereof.

In some embodiments, the oil comprises diisopropyl adipate and/or diethyl sebacate and/or dibutyl sebacate. In these embodiments, the diisopropyl adipate and/or diethyl sebacate and/or dibutyl sebacate are preferably present in a total amount of at least 60 wt % by weight of the discontinuous phase, more preferably at least 70 wt %, still more preferably at least 75 wt %. Preferably, the diisopropyl adipate and/or diethyl sebacate and/or dibutyl sebacate are present in a total amount of at most 80 wt % by weight of the discontinuous phase. Preferably the oil comprises diisopropyl adipate, more preferably in the aforementioned amounts. These preferred oils have been found to have a good solubility profile for crisaborole. Nevertheless, it is known to be difficult to obtain stable dispersions where these oils are used as a high proportion of the oil phase. Surprisingly, the present inventors have found that these oils can be incorporated as a high proportion of the discontinuous phase in the present invention.

In these embodiments, in addition to the diisopropyl adipate and/or diethyl sebacate and/or dibutyl sebacate, the oil preferably further comprises caprylic/capric triglycerides and/or castor oil, more preferably caprylic/capric triglycerides. The caprylic/capric triglycerides and/or castor oil increase the viscosity of the diisopropyl adipate and/or diethyl sebacate and/or dibutyl sebacate, thereby improving its processability. It may also improve the physical stability of the composition especially when low levels of surfactant are used. Surprisingly and unexpectedly, the inclusion of caprylic/capric triglycerides has been found to provide improved dermal diffusion of the active in an in vitro model, as shown in Example 6. In some embodiments, the oil comprises or consists of diisopropyl adipate and caprylic capric triglycerides.

Preferably, the oil comprises diisopropyl adipate and/or diethyl sebacate and/or dibutyl adipate. In these embodiments, the diisopropyl adipate and/or diethyl sebacate and/or dibutyl adipate are preferably present in a total amount of at least 60 wt % by weight of the discontinuous phase, more preferably at least 70 wt %, still more preferably at least 75 wt %. Preferably, the diisopropyl adipate and/or diethyl sebacate and/or dibutyl adipate are present in a total amount of at most 80 wt % by weight of the discontinuous phase. Preferably the oil comprises diisopropyl adipate, more preferably in the aforementioned amounts. These preferred oils have been found to have a good solubility profile for crisaborole and achieve good dermal diffusion of the active in an in vitro model, as shown in Example 6. Nevertheless, it is known to be difficult to obtain stable dispersions where these oils are used as a high proportion of the oil phase. Surprisingly, the present inventors have found that these oils can be incorporated as a high proportion of the discontinuous phase in the present invention.

In these embodiments, in addition to the diisopropyl adipate and/or diethyl sebacate and/or dibutyl adipate, the oil preferably further comprises caprylic/capric triglycerides and/or castor oil, more preferably caprylic/capric triglycerides. The effects of these additional oils are explained above. Preferably, the oil consists essentially of or consists of the diisopropyl adipate and/or diethyl sebacate and/or dibutyl adipate, and, where present, the caprylic/capric triglycerides and/or castor oil. Preferably the caprylic/capric triglycerides and/or castor oil are present in a total amount of at least 10 wt % by weight of the discontinuous phase, preferably at least 25 wt %.

In certain especially preferred embodiments, the oil comprises, by weight of the composition:
 (i) diisopropyl adipate in an amount of from 5 to 45 wt %;
 (ii) diethyl sebacate and/or dibutyl adipate in a total amount of from 5 to 45 wt %; and
 (iii) castor oil and/or caprylic/capric triglycerides in a total amount of from 5 to 45 wt %.

Preferably the oil consists essentially of or consists of components (i) to (iii), preferably in the aforementioned amounts.

In certain especially preferred embodiments, the oil comprises, by weight of the composition:
 (i) diisopropyl adipate in an amount of from 5 to 45 wt %;
 (ii) diethyl sebacate in a total amount of from 5 to 45 wt %; and
 (iii) caprylic/capric triglycerides in a total amount of from 5 to 45 wt %.

Preferably the oil consists essentially of or consists of components (i) to (iii), preferably in the aforementioned amounts.

Another strategy developed by the inventors for achieving good solvation of the crisaborole at high crisaborole concentrations is to incorporate a significant proportion of polar water-miscible solvent into the continuous phase and to solvate the crisaborole in the continuous phase. Thus, in some embodiments, the continuous phase comprises at least 50 wt %, preferably at least 60 wt %, more preferably at least 70 wt %, and most preferably at least 80 wt % by weight of the continuous phase of a polar water-miscible solvent selected from the group consisting of $C_1$-$C_4$ alcohols, polyethylene glycol, ethylene glycol, propylene glycol, butylene glycol, pentylene glycol, glycerol, diethylene glycol mono ethyl ether, propylene carbonate and mixtures of two or more thereof. Preferably, the continuous phase comprises at most 90 wt % of said solvents. In these embodiments, the continuous phase is aqueous and is preferably present in an amount of at least 30 wt % by weight of the composition, more preferably at least 40 wt %, still more preferably at least 50 wt %. In these embodiments, the crisaborole is predominantly in the continuous phase. As shown in Example 7, crisaborole is susceptible to degradation when exposed to an aqueous medium. Without wishing to be bound by theory, the present inventors believe that the incorporation of a significant proportion of polar water miscible-solvent into the continuous phase serves to suppress the water activity (Aw) of the continuous phase while keeping the active solvated, thereby improving the chemical stability of the composition relative to the emulsion-based formulations of the prior art.

In these embodiments, the discontinuous phase comprises an oil, preferably selected from mineral oil, dimethicone, cyclomethicone, heptamethyl nonane, hydrogenated polyisobutene, heptamethyl nonane and mixtures of two or more thereof. It has been found that where high levels of polar non-aqueous solvent are included in the composition and the crisaborole is solvated in the continuous phase, oils that have a relatively poor solubility profile for crisaborole are more effective at preserving the physical stability of the composition. Without wishing to be bound by theory, the present inventors believe that oils having a relatively poor solubility profile for crisaborole have less of a tendency to be dissolved themselves within the aqueous phase.

Preferably, the composition of the present invention comprises at least 10 wt % water by weight of the composition, more preferably at least 20 wt %. Preferably, the composition comprises at most 60 wt % water by weight of the composition, more preferably at most 40 wt %.

Preferably, the composition of the present invention comprises a surfactant. The surfactant may be incorporated into the discontinuous phase and/or the continuous aqueous phase. Suitable surfactants include an alkyl polyglycol ether, an alkyl polyglycol ester, an ethoxylated alcohol, a polyoxyethylene sorbitan fatty acid ester, a polyoxyethylene fatty acid ester, an ionic or non-ionic surfactant, a hydrogenated castor oil/polyoxyethylene glycol adduct containing from 25 to 60 ethoxy groups, a castor oil/polyoxyethylene glycol adduct containing from 25 to 45 ethoxy groups, a sorbitan fatty acid ester (for example Span 20 or Span 80), a block copolymer of ethylene oxide and propylene oxide (for example Pluronic L121 or Pluronic F68), or a mixture thereof. It will be understood that other suitable surfactants may be used.

Preferably, the composition comprises two or more surfactants, for example a first surfactant incorporated into the discontinuous phase, and a second, different surfactant incorporated into the continuous phase. The first and second surfactants are preferably selected from the list above. The first surfactant readily dissolves or disperses in the discontinuous phase and is preferably selected from the group consisting of Laureth-4 (polyoxyethylene (4) monododecyl ether), polysorbate 80, Span 80, and mixtures of two or more thereof. The second surfactant readily dissolves or disperses in the continuous phase and is preferably selected from the group consisting of Polysorbate 20, Pluronic L121, Pluronic F68, PEG-40 hydrogenated castor oil, Span20 and mixtures of two or more thereof. Most preferably, the first surfactant is Laureth-4 (polyoxyethylene (4) monododecyl ether), and the second surfactant is Polysorbate 20.

Preferably, the composition has a total surfactant content of less than 5 wt % by weight of the composition, more preferably less than 3 wt %, still more preferably less than 2 wt %, still more preferably less than 1 wt %, and most preferably less than 0.5 wt %. Preferably, the total surfactant content is at least 0.1 wt %. The use of low levels of surfactant is facilitated by the use of the polyaphron dispersions described herein and minimises the skin irritancy caused by the composition. This is especially advantageous where the patient already has inflamed skin.

Optionally, the composition further comprises a second discontinuous phase. In this embodiment, the second discontinuous phase is physically distinct from the first discontinuous phase. The second discontinuous phase may, for example, comprise agents such as emollient oils (to improve in use 'feel'), occlusive oils to prevent skin dehydration and to enhance skin permeation by the active, agents that provide a heating or cooling sensation when applied to the skin or sunscreens. Preferably, the second discontinuous phase comprises or consists of mineral oil. Preferably, the second discontinuous phase is present in an amount of from 10 to 30 wt % by weight of the composition, more preferably from 15 to 25 wt %.

Preferably, the composition of the present invention is dispersible in water. Preferably the composition of the present invention is dilutable in water. This increases the flexibility of use of the invention, for example in improving the application of the composition to the scalp through hair by leaving the hair wet, or from rinsing the preparation from any topical surface should the desire or need arise, or by the easy removal by rinsing of product from accidental contamination of clothing. These advantages improve the in-use experience of users and improve patient compliance.

Preferably, the composition of the present invention further comprises a gelling agent and/or a rheology modifying agent, such as a viscosity modifier. The gelling agent may, for example, be selected from alginate gums or their salts, guar gum, locust bean gum, xanthan gum, gum acacia, gelatin, hydroxymethylcellulose, hydroxyethylcellulose, hydroxypropylcellulose, carboxymethylcellulose or its salts, bentonites, magnesium aluminium silicates, "Carbomers" (salts of cross-linked polymers of acrylic acid), or glyceryl polymethacrylates or their dispersions in glycols. It will be understood that other suitable gelling agents may be used. Additionally, it has been found that some of the gelling agents (for example, carbomers) may also function as a chemical buffering agents thus preventing unwanted variation in the pH of the composition during storage and use. Where a viscosity modifier is used, this is preferably a polymeric cellulosic thickener. The inclusion of a gelling agent and/or rheology modifying agent provides additional stability against creaming and ensures that the active concentration is uniform throughout the composition. The use of these components is described in WO97/32559. The choice of gelling/thickening agents also allows for control of formulation viscosity from a thin lotion that is readily pourable to a thick cream with a significant resistance to flow.

Preferably, the composition of the present invention comprises from 0.05 to 5.0% by weight of a gelling agent, preferably from 0.1 to 2.0% by weight and more preferably from 0.2 to 1.0% by weight of the composition. In one embodiment of the present invention the composition has the consistency of a gel.

The compositions of the present invention may also contain other additives such as preservatives (for instance to prevent microbiological spoilage), buffering agents (for the control of pH and to avoid instability and damage to the skin's acid mantle) and antioxidants. Where a preservative is used, it is preferably present in an amount of from 0.1 to 1 wt %, more preferably 0.5 to 1 wt %, still more preferably from 0.6 to 0.8 wt %, by weight of the composition. The preservative is preferably benzyl alcohol or phenoxyethanol, more preferably phenoxyethanol. These additives may be included in the continuous or the discontinuous phase of the polyaphron dispersion. It will be understood that the inclusion of these additives will be at the levels and with the type of materials which are found to be effective and useful. Care needs to be taken in the choice and amount of these additives to prevent compromise to the other performance advantages of the present invention.

Preferably, the composition further comprises at least one pharmaceutically acceptable excipient. Suitable excipients for topical compositions are known in the art and include agents that repair any skin damage that results from the application of the composition.

Preferably, the composition has a pH of from about 4 to about 6.5, more preferably from about 5 to about 6, and most preferably about 5.5. As shown in Example 7, crisaborole has optimal stability in aqueous solution within these ranges. It will be understood that any suitable acid or base may be used to adjust the pH to the appropriate value or pH range. Typically the pH of the composition will need to be raised by the addition of a base, which suitably may be triethanolamine. Other suitable bases include, but are not limited to trishydroxymethylaminomethane (tris), sodium hydroxide and potassium hydroxide. Advantageously and preferably, the pH of the composition may be stabilized by the incorporation of a suitable buffer into the aqueous phase. Suitable buffer systems having a pH within the specified range will be familiar to those skilled in the art.

Preferably, the composition is chemically stable for at least 12 months at 5° C.±3° C., as measured at 60% RH±5%. The stability is measured after storage in a closed, airtight glass container with headspace comprising no more than 5% by volume of the total usable volume of the container. By "chemically stable" it is meant an HPLC assay for crisaborole of 100%±5% relative to the measurement at t=0.

Preferably, the composition is chemically stable for at least 12 months at 25° C.±2° C., as measured at 60% RH±5%. The stability is measured after storage in a closed, airtight glass container with headspace comprising no more than 5% by volume of the total usable volume of the container. Again, by "chemically stable" it is meant an HPLC assay for crisaborole of 100%±5% relative to the measurement at t=0.

Preferably, the composition is chemically stable for at least 6 months at 40° C.±3° C. The stability is measured after storage in a closed, airtight glass container with headspace comprising no more than 5% by volume of the total usable volume of the container. "Chemically stable" takes the same meaning as above.

Preferably, the composition is physically stable for at least 12 months at 5° C. 3° C., as measured at 60% RH±5%. The stability is measured after storage in a closed, airtight glass container with headspace comprising no more than 5% by volume of the total usable volume of the container. By "physically stable" it is meant that the composition appears as a homogeneous cream with no gross apparent rheological or appearance changes from t=0. Preferably, by "physically stable" it is also meant that the composition does not appear to contain crystals or solid particulates when viewed under a microscope, and/or that the composition has a particle size distribution profile that has undergone no significant changes from t=0. The particle size distribution can be determined by microscopy or laser diffraction, such as using a Malvern Mastersizer 2000 or Malvern Mastersizer 3000.

Preferably, the composition is physically stable for at least 12 months at 25° C. 2° C., as measured at 60% RH±5%. The stability is measured after storage in a closed, airtight glass container with headspace comprising no more than 5% by volume of the total usable volume of the container. Again, by "physically stable" it is meant that the composition appears as a homogeneous cream with no gross apparent rheological or appearance changes from t=0, and preferably that the composition does not appear to contain crystals or solid particulates when viewed under a microscope, and/or that the composition has a particle size distribution profile that has undergone no significant changes from t=0.

Preferably, the composition is physically stable for at least 6 months at 40° C.±3° C., as measured at 60% RH±5%. The stability is measured after storage in a closed, airtight glass container with headspace comprising no more than 5% by volume of the total usable volume of the container. "Physically stable" takes the same meaning as above.

In these embodiments, the glass container is preferably evacuated prior to the storage of the composition.

In an especially preferred embodiment the composition comprises, by weight of the composition:
from 2 to 4 wt % crisaborole, and
at least 60 wt % discontinuous phase comprising an oil;
wherein the crisaborole is predominantly in the discontinuous phase,
wherein the oil comprises at least 60 wt % diisopropyl adipate by weight of the discontinuous phase, and
wherein the composition is in the form of a lotion or cream.

In a further especially preferred embodiment the composition comprises from 1.5 to 5 wt % crisaborole by weight of the composition, and a discontinuous phase comprising an oil, wherein the crisaborole is predominantly in the discontinuous phase, wherein the oil comprises, by weight of the composition:
(i) diisopropyl adipate in an amount of from 5 to 45 wt %;
(ii) diethyl sebacate and/or dibutyl adipate in a total amount of from 5 to 45 wt %; and
(iii) castor oil and/or caprylic/capric triglycerides in a total amount of from 5 to 45 wt %.

In a further especially preferred embodiment the composition comprises, by weight of the composition:
from 2 to 4 wt % crisaborole, and
at least 40 wt % continuous aqueous phase;
wherein the crisaborole is predominantly in the continuous aqueous phase,
wherein the continuous aqueous phase comprises at least 60 wt % propylene glycol by weight of the continuous aqueous phase, and
wherein the composition is in the form of a lotion or cream.

In a further especially preferred embodiment the composition comprises, by weight of the composition:
from 1.5 to 5 wt % crisaborole, and
at least 40 wt % continuous aqueous phase;
wherein the crisaborole is predominantly in the continuous aqueous phase,
wherein the continuous aqueous phase comprises at least 50 wt %, preferably at least 60 wt % by weight of the continuous phase of a polar water-miscible solvent selected from the group consisting of $C_1$-$C_4$ alcohols, polyethylene glycol, ethylene glycol, propylene glycol, butylene glycol, pentylene glycol, glycerol, diethylene glycol mono ethyl ether, propylene carbonate and mixtures of two or more thereof.

According to a further aspect, there is provided a composition as described herein for use in the treatment of the human or animal body by therapy.

According to a further aspect, there is provided a method of treatment of the human or animal body by therapy, the method comprising administering to a subject in need thereof an effective amount of a composition as described herein.

According to a further aspect, there is provided the use of a composition as described herein for the manufacture of a medicament for the treatment of a human or animal subject by therapy.

According to a further aspect, there is provided a composition as described herein for use in the treatment of atopic dermatitis or psoriasis.

According to a further aspect, there is provided a method of treating atopic dermatitis or psoriasis in a human or animal subject comprising administering to a subject in need thereof an effective amount of a composition as described herein.

According to a further aspect, there is provided the use of a composition as described herein for the manufacture of a medicament for the treatment of atopic dermatitis or psoriasis in a human or animal subject.

The composition as described herein can also be used to treat other inflammatory dermatological conditions.

The composition as described herein may be applied to the scalp or other skin surface through hair. Preferably in this embodiment the hair is wetted (for example by use of water with or without shampoo, and then towel dried). The product may then be applied to the scalp in a suitable amount and then massaged into the scalp through the hair. The hair may then be left to dry naturally or dried using a hair dryer. Advantageously, the water-dispersible form of the formulation enables an even distribution of the actives on the skin using this process. Alternatively, or additionally, the composition may be massaged into the scalp through dry hair and left for a suitable period (which may be 8 to 12 hours) after which the excess or reminder may be rinsed out with water with or without shampoo. Preferably the composition is applied to a human or animal in unit dosage form.

According to a further aspect, there is provided a package comprising the composition described herein. Preferably, the package is a tube or an airless pump. For example, a tube can be squeezed for topical application of the composition.

According to a further aspect, there is provided a method for manufacturing a composition, the method comprising:
 (i) providing a hydrophilic solvent, optionally comprising crisaborole and/or a surfactant;
 (ii) providing a hydrophobic solvent, optionally comprising crisaborole and/or a surfactant; and
 (iii) mixing the hydrophilic solvent with the hydrophobic solvent under suitable conditions to form a composition for topical application comprising a polyaphron dispersion, wherein the polyaphron dispersion comprises a continuous phase, a discontinuous phase and crisaborole.

Preferably, the composition produced by the method is the composition as described above. Suitable methods for preparing polyaphron dispersions are described in U.S. Pat. No. 4,486,333. It will be understood by those skilled in the art that other manufacturing methods may be used, as appropriate.

Preferably, the method further comprises packaging the composition.

The present invention will now be described in relation to the following non-limiting figures.

The present invention will now be described in relation to the following non-limiting examples.

EXAMPLE 1

10 grams of a composition for topical application in accordance with the present invention was prepared by combining the following components:

8.75 g polyaphron dispersion
1.1 g gel mix
0.15 g NaOH (20% aq)
water q.s.

The polyaphron dispersion had the following composition:

|  | Wt in final (g) | % in final |
|---|---|---|
| Oil Phase |  |  |
| Crisaborole | 0.20 | 2.00 |
| Diisopropyl adipate | 5.00 | 50.00 |
| Capric/caprilic triglyceride | 2.00 | 20.00 |
| Laureth-4 | 0.07 | 0.70 |
| Aqueous phase |  |  |
| Polysorbate 20 | 0.015 | 0.15 |
| Water | 1.46 | 14.60 |
|  | 8.745 | 87.45 |

The polyaphron dispersion was prepared by mixing the oil phase components together in a vessel using 40° C. heating and stirred with a magnetic follower until fully dissolved. The mixture was then allowed to cool to room temperature. In a separate vessel the aqueous phase components were mixed using an overhead stirrer with a propeller style blade at 70 rpm. Once homogeneous the stirrer speed was increased to 300 rpm and the oil phase was slowly added over 20 minutes. The system was mixed for a further 20 minutes to ensure an even droplet sized distribution. The final polyaphron dispersion had the appearance of a white viscous cream.

The gel mix had the following composition:

|  | Quantity (g) | Wt in final (g) | % in final |
|---|---|---|---|
| Carbomer (Ultrez 10 | 2.08 | 0.02288 | 0.2288 |
| Natrosol 250L | 0.42 | 0.00462 | 0.0462 |
| Phenoxyethanol | 1.46 | 0.01606 | 0.1606 |
| Water | 96.04 | 1.05644 | 10.5644 |
|  | 100.00 | 1.100 | 11.00 |

The Natrosol, Phenoxyethanol and water were mixed using a magnetic follower and 40° C. heating until the Natrosol had fully dissolved. Still stirring the system was then allowed to cool and the carbomer was added. Mixing was continued until the carbomer was fully dispersed with no evidence of lumps.

The gel mix was then added to the polyaphron dispersion and mixed using an overhead stirrer (70 rpm) for 5 minutes before neutralization with the sodium hydroxide solution.

The resulting composition appeared to be stable with no signs of crystals under polarized light.

EXAMPLE 2

A composition for topical application comprising the following components was prepared:

| | | Quantity (g) | % in final |
|---|---|---|---|
| Polyaphron dispersion | Oil phase | | |
| | Mineral oil | 50.00 | 50.00 |
| | Aqueous phase | | |
| | Cremophor RH40 | 0.50 | 0.50 |
| | Propylene glycol | 7.80 | 7.80 |
| | Water | 4.20 | 4.20 |
| | | 62.50 | 62.50 |
| Gel phase | Crisaborole | 2.00 | 2.00 |
| | Propylene giycol | 24.70 | 24.70 |
| | Carbomer (Ultrez 10) | 0.50 | 0.50 |
| | Water | 12.00 | 12.00 |
| Adjust | Trolamine (50% a.q.) | q.s. | q.s. |
| | Water | q.s. | q.s. |
| | | 100.00 | 100.00 |

The polyaphron dispersion was made using the method of Example 1.

The gel phase was made by dispersing the carbomer in the water using a magnetic follower until the dispersion was fully solvated and free of lumps. In a separate vessel the crisaborole was dissolved in the propylene glycol using a magnetic follower. Under suitable mixing the two are then combined.

The polyaphron dispersion was then mixed into the gel phase and the trolamine/water was added to increase the pH to activate the thickener, thereby thickening the system.

The resulting composition appeared to be stable with no signs of crystals under polarized light.

EXAMPLE 3

A composition for topical application comprising the following components was prepared:

| | | Quantity (g) | % in final |
|---|---|---|---|
| API solution | Crisaborole | 2.00 | 2.00 |
| | Diethylene glycol morioethyl ether | 20.00 | 20.00 |
| Gel phase | Carbomer (Ultrez 10) | 0.50 | 0.50 |
| | Water | 15.00 | 15.00 |
| | Propylene glycol | 15.00 | 15.00 |
| Polyaphron dispersion | Oil phase | | |
| | Mineral oil | 19.34 | 19.34 |
| | Arlamol HD | 19.34 | 19.34 |
| | Aqueous phase | | |
| | Kolliphor RH40 | 0.387 | 0.387 |
| | Diethylene glycol monoethyl ether | 3.23 | 3.23 |
| | Water | 3.20 | 3.20 |
| Adjust (to pH5.5) | Neutrol TE (50% a.q.) | q.s. | q.s. |
| | Water | q.s. | q.s. |
| | | 100.00 | 100.00 |

The API solution was made by simple stirring with a magnetic follower (no heat required).

The gel phase was made by adding the carbomer to the water with gentle stirring until the carbomer was fully dispersed before addition of the propylene glycol.

| | |
|---|---|
| UPLC System | Waters Photodiode Array Detector |
| | Waters Acquity H-Class UPLC System |
| | Waters Empower3 Data Processing Software |
| Column | Waters Acquity UPLC CSH C18 1.7 um 2.1 × 100 mm |
| Guard Column | N/A |
| Detection | 251 nm |
| Sample Temperature | 5° C. |

The polyaphron dispersion was made as described in Example 1.

The final system was made by slowly adding the gel phase to the API solution, followed by the polyaphron dispersion, followed by the adjust phase. All carried out under moderate stirring.

The sample was stored in a closed, airtight glass container with headspace comprising no more than 5% by volume of the total usable volume of the container. Each container containing a sample was stored at a constant temperature of 40° C. in a standard laboratory incubator (for example, Memmert IF260PLUS Incubator). The storage period for each sample was three months.

The chemical stability of the crisaborole in each sample after the storage period was measured by a HPLC method. The HPLC method was as follows:

| | | | |
|---|---|---|---|
| Column Temperature | 40° C. | | |
| Flow Rate | 0.5 mL/min | | |
| Mobile Phase | Mobile Phase A: 0.2% Trifluoroacetic acid in Deionised Water | | |
| | Mobile Phase B: 100% Acetonitrile | | |
| | Time (min) | % A | % B |
| Gradient | 0 | 85 | 15 |
| | 1 | 85 | 15 |
| | 5 | 70 | 30 |
| | 25 | 60 | 40 |
| | 27 | 60 | 40 |
| | 27.1 | 85 | 15 |
| | 32 | 85 | 15 |
| Injection Volume | 2 µL | | |
| Run Time | 32 min | | |

Mobile Phase Preparation:

Mobile phase A: 2 mL of trifluoroacetic acid in 1 L of deionised water. Mix well before use.

Mobile phase B: 100% Acetonitrile

Sample Preparation for 2% Strength Formulation:

Acetonitrile is used as the sample diluent

Prepare all samples in amber glassware

Procedure:

1. Weigh 0.1 g (±0.012 g) of sample into 20 mL amber volumetric flask, minimizing sample on the neck of the flask.
2. Add diluent to volume, and mix by inversion.
3. Add a magnetic stirrer and stir for 1 hour at 400 rpm.
4. Filter through 0.45 µm PTFE syringe filter into amber HPLC vials.

Standard Preparation:

Acetonitrile is used as the sample diluent

Prepare all standards in amber glassware

A solution of crisaborole in acetonitrile at a target concentration of 100 µg/mL For Example 3, the crisaborole peak purity (i.e. the area of the peak of interest compared to the total area of all API related peaks in the chromatogram, expressed as a percentage) measured after storage for 3 months at 40° C. (see above) was 97.1%.

EXAMPLE 4

A composition for topical application comprising the following components was prepared:

| | | Quantity (g) | % in final |
|---|---|---|---|
| Polyaphron dispersion | Oil phase | | |
| | Crisaborole | 0.80 | 2.00 |
| | Diisopropyl adipate | 6.34 | 15.84 |
| | Diethyl sebacate | 6.33 | 15.83 |
| | Castor oil | 6.33 | 15.83 |
| | Butylated hydroxyanisole | 0.04 | 0.10 |
| | Laureth 4 | 0.20 | 0.50 |
| | Aqueous phase | | |
| | Poloxamer 407 | 0.25 | 0.62 |
| | Water | 4.71 | 11.78 |
| Unneutralised Gel | Carbomer Ultrez 10 | 0.30 | 0.75 |
| | Natrosol 250L | 0.08 | 0.20 |
| | Phenoxyethanol | 0.28 | 0.70 |
| | Water | 13.54 | 33.85 |
| | Sodium citrate dehydrate | 0.05 | 0.123 |
| | Citric acid (anhydrous) | 0.03 | 0.071 |
| | Water | 0.32 | 0.81 |
| Adjust (to pH 5.5) | Sodium hydroxide (20% aqueous solution) | q.s. | q.s. |
| | Water | q.s. | q.s. |
| | | 40.00 | 100.00 |

The composition was prepared using an analogous method to Example 1.

The crisaborole peak purity measured after storage for 3 months at 40° C. under the conditions described in Example 3 was 99.0%.

EXAMPLE 5

A composition for topical application comprising the following components was prepared:

| | | Quantity (g) | % in final |
|---|---|---|---|
| Polyaphron dispersion | Oil phase | | |
| | Crisaborole | 0.80 | 2.00 |
| | Diisopropyl adipate | 7.60 | 19.00 |
| | Diethyl sebacate | 7.60 | 19.00 |
| | Capric/caprylic triglycerides (Miglyol 810 ™) | 3.80 | 9.50 |
| | Butylated hydroxyanisole | 0.04 | 0.10 |
| | Laureth 4 | 0.20 | 0.50 |
| | Aqueous phase | | |
| | Poloxamer 407 | 0.25 | 0.62 |
| | Water | 4.71 | 11.78 |
| Unneutralised Gel | Carbomer Ultrez 10 | 0.30 | 0.75 |
| | Natrosol 250L | 0.08 | 0.20 |
| | Phenoxyethanol | 0.28 | 0.70 |
| | Water | 13.54 | 33.85 |
| | Sodium citrate dehydrate | 0.05 | 0.123 |
| | Citric acid (anhydrous) | 0.03 | 0.071 |
| | Water | 0.32 | 0.81 |
| Adjust (to pH 5.5) | Sodium hydroxide (20% aqueous solution) | q.s. | q.s. |
| | Water | q.s. | q.s. |
| | | 40.00 | 100.00 |

The composition was prepared using an analogous method to Example 1.

The crisaborole peak purity measured after storage for 3 months at 40° C. under the conditions described in Example 3 was 99.3%.

EXAMPLE 6

Certain formulations were tested in a Franz cell in vitro diffusion experiment though an artificial membrane. The membrane used was a Strat-M Membrane from Merck Millipore and is described as a synthetic, non-animal based model for transdermal diffusion testing that is predictive of diffusion in human skin. A solution of 75% propylene glycol and 25% water was used as the receptor phase. Cells with a surface area of 0.64 cm$^2$ and a receptor volume of approximately 2 cm$^3$ were used. Approximately 30 mg of formulation was applied at time 0 hours and the cells were stirred and incubated at 37° C. throughout. The receptor phase was sampled and replaced at 2, 4, 6, 8, 12 and 24 hours. Crisaborole concentration was determined by HPLC using a similar method to that of Example 3 but using the following parameters:

| | | | |
|---|---|---|---|
| UPLC System | Waters Photodiode Array Detector | | |
| | Waters Acquity H-Class UPLC System | | |
| | Waters Empower3 Data Processing Software | | |
| Column | Waters Acquity UPLC CSH C18 | | |
| | 1.7 um 2.1 × 100 mm | | |
| Guard Column | N/A | | |
| Detection | 251 nm | | |
| Sample Temperature | 5° C. | | |
| Column Temperature | 40° C. | | |
| Flow Rate | 0.5 mL/min | | |
| Mobile Phase | Mobile Phase A: 0.2% Trifluoroacetic acid in Deionised Water | | |
| | Mobile Phase B: 100% Acetonitrile | | |
| | Time (min) | % A | % B |
| Gradient | 0 | 68 | 32 |
| | 5 | 68 | 32 |
| Injection Volume | 2 µL for StratM diffusion | | |
| Run Time | 5 min | | |

Figure 2:
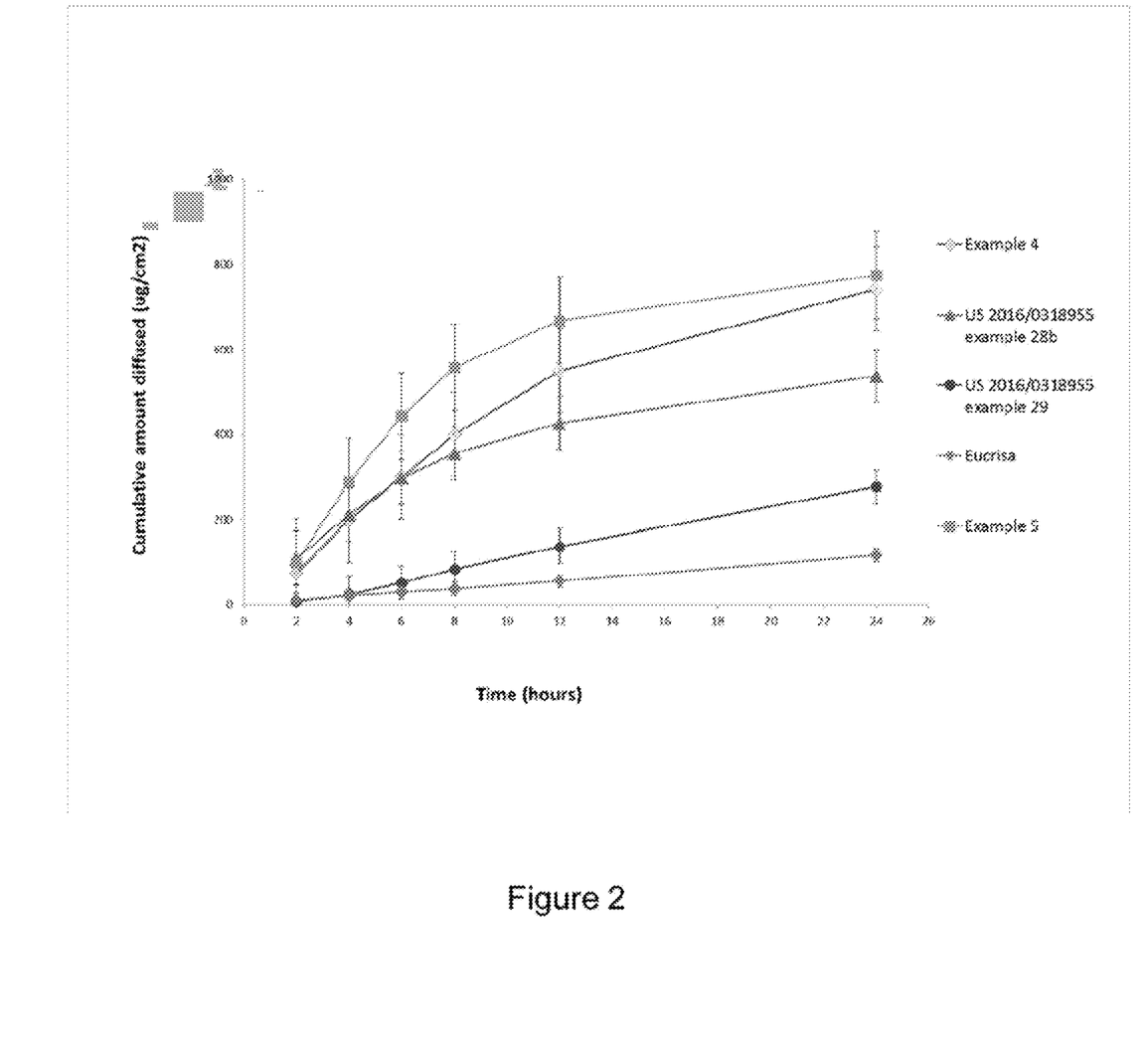
FIG. 2 is a graph showing the mean diffusion of the samples described in Example 6. The y-axis indicates mean cumulative crisaborole diffused in µg/cm$^2$. The error bars indicate standard error. In the data points, the diamond (unfilled) represents Example 4 described herein, the triangle represents the sample based on Example 28b of US 2016/0318955, the circle represents the sample based on Example 29 of US 2016/0318955, the diamond (filled) represents the commercially available Eucrisa® ointment, and the square represents Example 5 described herein.

Mean cumulative crisaborole per cm$^2$ of membrane for each sample was then plotted (see FIG. 2). The formulations tested were Examples 4 and 5 described herein, two formulations disclosed in US 2016/0318955 (Examples 28B and 29, but with the boron-based active agent replaced with crisaborole) and a commercially available Eucrisa® ointment (all having a crisaborole content of 2.0 wt %).

It can be seen from FIG. 2 that the polyaphron dispersion-based formulations (Examples 4 and 5 described herein) are superior in terms of in vitro diffusion properties to the emulsion-based formulations based on those disclosed in US 2016/0318955 and the Eucrisa® ointment. Of the two polyaphron dispersion-based formulations, Example 5—in which the castor oil of Example 4 was replaced with capric/caprylic triglycerides—exhibited greater efficacy.

EXAMPLE 7

A 1% solution of crisaborole was prepared with 50% ethanol and a citrate buffer to pH 5.5. The system was then stored at 40° C. for one month under the conditions of Example 3 and gave an 84% peak purity. Equivalent solutions were prepared and tested at pH 4.5, 6.5, 7.5 and 8.5. The results are shown in the following table:

| pH | % peak purity |
|---|---|
| 4.5 | 79.5 |
| 5.5 | 84.1 |
| 6.5 | 79.8 |
| 7.5 | 72.1 |
| 8.5 | 51.3 |

The results show that crisaborole is vulnerable to degradation when exposed to an aqueous medium and that its chemical stability is highest at pH 5.5.

EXAMPLE 8

The formulations of Example 5 described herein, and crisaborole equivalents of Examples 28B and 29 of US 2016/0318955 were tested for their chemical and physical stability. The samples were stored at room temperature for 24 hours in a closed, airtight glass container with headspace comprising no more than 5% by volume of the total usable volume of the container. The samples were then analysed using the HPLC method of Example 3. The percentages of two impurity peaks are shown in the following table:

| | Percentage area of impurity | |
|---|---|---|
| | RRT 0.73 | RRT 0.92 |
| US 2016/0318955 Example 28B | 0.07 | 1.34 |
| US 2016/0318955 Example 29 | 1.02 | 0.65 |
| Example 5 | 0.06 | 0.27 |
| Standard | — | 0.02 |

As shown in the table, the sample based on Example 29 of US 2016/0318955 was the most unstable sample tested with not only additional impurities but also having crystals evident under the microscope. The two observations may be related as the crystals will be exposed to water as they are not encapsulated within the oil phase (c.f. Example 7). This may explain why the impurity at relative retention time (RRT) 0.73 is significantly higher than the other formulas. The impurity detected at 0.73RRT is believed to be a degradation impurity related to aqueous exposure.

The sample based on Example 28B of US 2016/0318955 was found to exhibit a high level of the impurity at RRT 0.92. The cause of this impurity is, at present, unknown.

In parallel, samples were stored for 2 months at 4° C. For the sample based on Example 28B of US 2016/0318955 (crisaborole equivalent), amorphous solid lumps were observed to develop over time when examined under a microscope. These lumps were significantly different in appearance to those observed almost immediately in the sample based on Example 29 of US 2016/0318955 (see above). These amorphous solid lumps were not observed in the other samples.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

The invention claimed is:

1. A composition for topical application comprising a polyaphron dispersion, wherein the polyaphron dispersion comprises a continuous phase, a discontinuous phase and crisaborole,
   wherein the discontinuous phase comprises an oil, and
   wherein the oil comprises diisopropyl adipate and/or diethyl sebacate and/or dibutyl adipate.

2. A composition according to claim 1, wherein the crisaborole is present in an amount of from 1 to 5 wt % by weight of the composition.

3. A composition according to claim 1, wherein the crisaborole is predominantly in the discontinuous phase, or wherein the crisaborole is predominantly in the continuous phase.

4. A composition according to claim 1, wherein the discontinuous phase is present in an amount of at least 50 wt % by weight of the composition.

5. A composition according to claim 1, wherein the diisopropyl adipate and/or diethyl sebacate and/or dibutyl adipate are present in a total amount of at least 60 wt % by weight of the discontinuous phase.

6. A composition according to claim 1, wherein the discontinuous phase comprises an oil, and the oil comprises, by weight of the composition:
   (i) diisopropyl adipate in an amount of from 5 to 45 wt %;
   (ii) diethyl sebacate and/or dibutyl adipate in a total amount of from 5 to 45 wt %; and
   (iii) castor oil and/or caprylic/capric triglycerides in a total amount of from 5 to 45 wt %.

7. A composition according to claim 1, wherein the continuous phase comprises at least 50 wt % by weight of the continuous phase of a polar water-miscible solvent selected from the group consisting of $C_1$-$C_4$ alcohols, polyethylene glycol, ethylene glycol, propylene glycol, butylene glycol, pentylene glycol, glycerol, diethylene glycol mono ethyl ether, propylene carbonate and mixtures of two or more thereof.

8. A composition according to claim 1, having a total surfactant content of less than 5 wt % by weight of the composition.

9. A composition according to claim 1, wherein the composition comprises at least 10 wt % water by weight of the composition.

10. A composition according to claim 1, wherein the composition is in the form of a lotion or cream.

11. A composition according to claim 1, wherein at least 95 wt % of the crisaborole is dissolved in the composition.

12. A composition according to claim 1, wherein the composition is chemically and/or physically stable for at least 12 months at 25° C.±2° C., as measured at 60% RH±5%; and/or wherein the composition is chemically and/or physically stable for at least 6 months at 40° C.±3° C., as measured at 60% RH±5%.

13. A composition according to claim 1, comprising, by weight of the composition:
   from 2 to 4 wt % crisaborole, and
   at least 60 wt % discontinuous phase comprising an oil;
   wherein the crisaborole is predominantly in the discontinuous phase,
   wherein the oil comprises at least 60 wt % diisopropyl adipate by weight of the discontinuous phase, and
   wherein the composition is in the form of a lotion or cream.

14. A composition according to claim 1, comprising, by weight of the composition:
- from 2 to 4 wt % crisaborole, and
- at least 40 wt % continuous aqueous phase;
- wherein the crisaborole is predominantly in the continuous aqueous phase,
- wherein the continuous aqueous phase comprises at least 60 wt % propylene glycol by weight of the continuous aqueous phase, and
- wherein the composition is in the form of a lotion or cream.

15. A composition according to claim 1, for use in the treatment of the human or animal body by therapy.

16. A composition according to claim 1 for use in the treatment of atopic dermatitis or psoriasis.

17. A composition according to claim 1, wherein the crisaborole is present in an amount of from 2 to 4 wt % by weight of the composition.

18. A composition according to claim 1, having a total surfactant content of less than 1 wt % by weight of the composition.

19. A composition according to claim 1, having a total surfactant content of less than 0.5 wt % by weight of the composition.

\* \* \* \* \*